US00PP27715P2

(12) United States Plant Patent
Hachmann

(10) Patent No.: US PP27,715 P2
(45) Date of Patent: Feb. 28, 2017

(54) ***DASIPHORA* PLANT NAMED 'HACHLISS'**

(50) Latin Name: ***Dasiphora fruticosa* subsp. *fruticosa***
Varietal Denomination: Hachliss

(71) Applicant: Holger Hachmann, Barmstedt (DE)

(72) Inventor: Holger Hachmann, Barmstedt (DE)

(73) Assignee: HACHMANN BAUMSCHULEN, Barmstedt (DE)

( * ) Notice: Subject to any disclaimer, the term of this patent is extended or adjusted under 35 U.S.C. 154(b) by 118 days.

(21) Appl. No.: 14/544,421

(22) Filed: Jan. 5, 2015

(51) Int. Cl.
*A01H 5/02* (2006.01)

(52) U.S. Cl.
USPC ..... Plt./237

(58) Field of Classification Search
USPC ..... Plt./237
See application file for complete search history.

(56) References Cited

PUBLICATIONS

CPVO Community Plant Variety Office Feb. 2014, Apr. 15, 2014 retrieved on Jun. 21, 2016, retrieved from the Internet at <http://www.cpvo.europa.eu/documents/gazettes/2014/cpvo_2014_2.pdf> pp. cover page, 32 and 52.*

Canadian Food Inspection Agency 2016 *Hachliss* retrieved on Jun. 21, 2016, retrieved from the Internet at <http://www.inspection.gc.ca/english/plaveg/pbrpov/cropreport/ptt/app00009441e.shtml> 2 pp.*

* cited by examiner

*Primary Examiner* — June Hwu
(74) *Attorney, Agent, or Firm* — Penny J. Aguirre

(57) ABSTRACT

A new cultivar of *Dasiphora* plant, 'Hachliss', that is characterized by its compact, bushy, and dwarf plant habit, its very floriferous blooming habit; blooming from July to September in Germany, it flowers that are deep red-pink in color, and its resistance to powdery mildew and red spider mites.

2 Drawing Sheets

Botanical classification: *Dasiphora fruticosa* subsp. *fruticosa.*

Variety denomination: 'Hachliss'.

BACKGROUND OF THE INVENTION

The present invention relates to a new and distinct cultivar of *Dasiphora fruticosa* subsp. *fruiticosa*. The new cultivar will be referred to hereafter by its cultivar name, 'Hachliss'. 'Hachliss' is a new cultivar of shrubby cinquefoil grown for use as a landscape shrub.

The new cultivar is the result of a controlled breeding program conducted by the Inventor in Barmstedt, Germany. The intent of the breeding program is to develop new cultivars of *Dasiphora* with brightly colored flowers. The new cultivar arose from a cross made by the Inventor in Barmstedt, Germany in summer of 2003 between the cultivars 'Rosiflor' (not patented) as the female parent and 'Red Ace' (not patented) as the male parent. The Inventor selected 'Hachliss' as a single unique plant amongst the seedlings that resulted from the above cross in July of 2006.

Asexual propagation of the new cultivar was first accomplished by the Inventor by softwood stem cuttings in Barmstedt, Germany in 2012. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hachliss' as a unique cultivar of *Dasiphora.*

1. 'Hachliss' exhibits a compact, bushy, and dwarf plant habit.
2. 'Hachliss' exhibits a very floriferous blooming habit; blooming from July to September in Germany.
3. 'Hachliss' exhibits flowers that are deep red-pink in color.
4. 'Hachliss' has been observed to be resistant to powdery mildew (*Podosphaera aphanis*) and red spider mites (*Tetranychus urticae*) on trials to date.

The female parent of 'Hachliss', 'Rosiflor', differs from 'Hachliss' in having smaller flowers that are bluish pink in color and in having a taller more uneven plant habit. The male parent of 'Hachliss', 'Red Ace', differs from 'Hachliss' in having a more vigorous growth rate and in having red colored flowers that fade quickly after opening. 'Hachliss' can be most closely compared to the *Dasiphora* cultivars 'Pretty Polly' (not patented) and 'Pink Beauty' (U.S. Plant Pat. No. 9,874). 'Pretty Polly' differs from 'Hachliss' in having flowers that are bluish pink in color, in having a prostrate plant habit, and in having a less floriferous blooming habit. 'Pink Beauty' differs from 'Hachliss' in having semi-double salmon pink colored flowers, in having an upright plant habit, and in having a less floriferous blooming habit.

BRIEF DESCRIPTION OF THE DRAWINGS

The accompanying colored photographs illustrate the overall appearance and distinct characteristics of the new *Dasiphora*, 'Hachliss'. The photographs were taken of two year-old plants as grown outdoors in two-liter containers in Barmstedt, Germany.

The photograph in FIG. 1 provides a view of the overall plant habit of 'Hachliss'.

Figure 1:
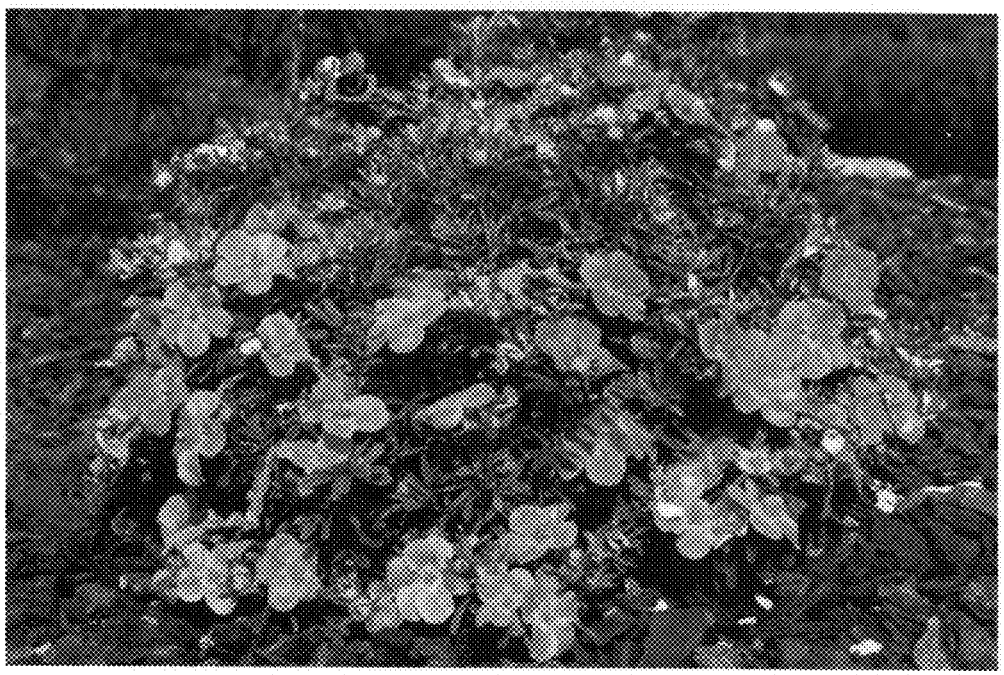
Figure 2:
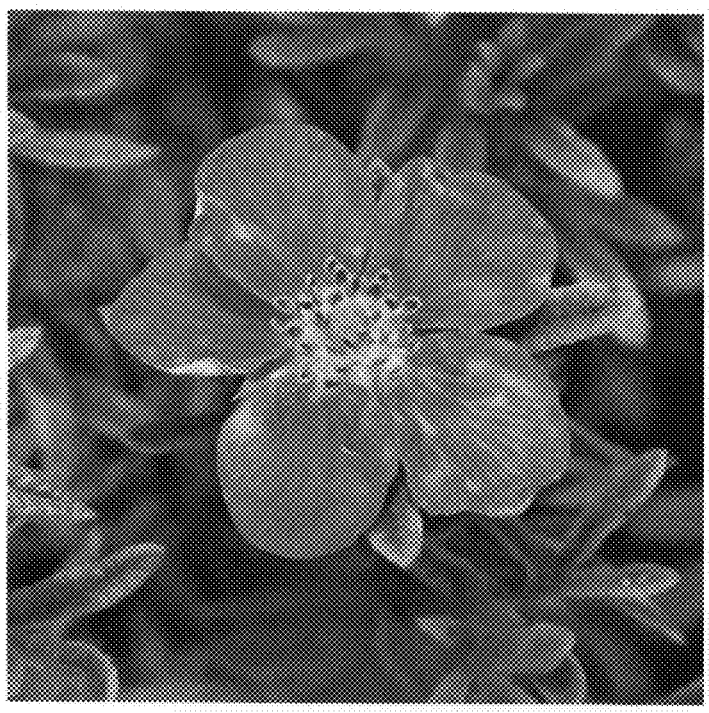

The photograph in FIG. 2 provides a close-up view of a mature flower of 'Hachliss'.

Figure 3:
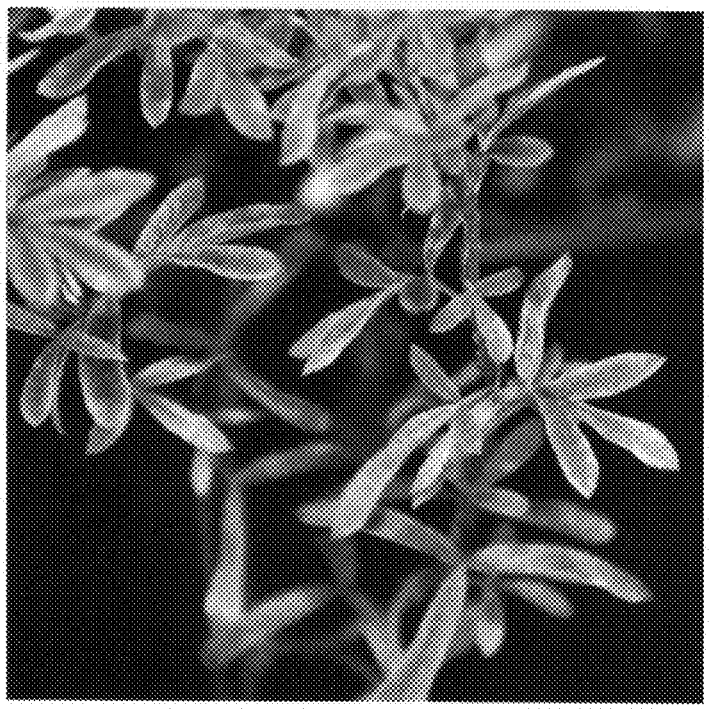

The photograph in FIG. 3 provides a close-up view of the foliage of 'Hachliss'.

The colors in the photographs are as close as possible with digital photography techniques available, the color values cited in the detailed botanical description accurately describe the colors of the new *Dasiphora*.

DETAILED BOTANICAL DESCRIPTION

The following is a detailed description of two year-old plants of the new cultivar as grown outdoors in two-liter containers in Barmstedt, Germany. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Twelve weeks from July to September in Barmstedt, Germany.

*Plant type.*—Perennial, deciduous shrub.

*Plant habit.*—Compact, bushy, and dwarf plant habit.

*Height and spread.*—An average of 50 cm in height and width.

*Cold hardiness.*—At least to U.S.D.A. Zone 3.

*Diseases and pests.*—Resistance to powdery mildew (*Podosphaera aphanis*) and red spider mites (*Tetranychus urticae*) has been observed.

*Propagation*—Softwood stem cuttings.

*Root description*—Fibrous and fine.

*Growth rate.*—Slow.

*Crop time to produce a flowering plant.*—About 15 months from a rooted cutting to fully develop a flowering plant in a 2-liter container.

Branch description:

*Stem shape.*—Rounded.

*Stem color.*—Young; 145B, mature wood; 174A to 174B.

*Stem surface* (*young and mature*).—Dull and moderately covered with short, soft hairs; an average of 1 mm in length and 157D in color.

*Branching.*—Freely branching, an average of 40 lateral branches.

*Stem size.*—An average of 15.6 cm in length and 2 mm in diameter.

*Stem strength.*—Very strong.

*Stem aspect.*—Stems grow in all directions from nearly horizontal to vertical.

Foliage description:

*Leaves.*—Compound, trifoliate to palmate division, broadly ovate in overall shape, alternate arrangement, an average of 1.6 cm in length and 2.4 cm in width, an average of 18 leaves per branch, internode length an average of 9 mm.

*Leaflets.*—3 to 5, narrow obovate to oblanceolate in shape, about 60% of trifoliate leaf center leaflets are trifid, giving those leaves a palmate-like overall leaf shape, acute to short apiculate apex, attenuate base, entire margin, an average of 1.3 cm in length and 2.5 mm in width, color; young upper surface 143A, young lower surface 147B, mature upper surface 137A, mature lower surface 191B, upper and lower surface slightly glossy with upper surface very sparsely pubescent and lower surface and margins sparsely pubescent; hairs an average of 1 mm in length and 157D in color.

*Venation.*—Leaves; palmate, leaflets; pinnate, color; upper surface 147A, lower surface 147C.

*Stipules.*—Ovate in shape, an average of 7 mm in length and 2 mm in width, color of upper and lower surface N199D, surface sparsely pubescent.

*Petioles.*—An average of 4 mm in length and 0.5 mm in diameter, 143B in color, leaflets sessile, surface sparsely pubescent.

Inflorescence description:

*Inflorescence type.*—Solitary, pairs, and clusters, terminally and axillary placed along the stems.

*Flower number.*—An average of 12 per main stem.

*Flower fragrance.*—None.

*Flower longevity.*—About 5 days, self-cleaning.

*Flower type.*—Single, rotate.

*Flower aspect.*—Upright to outward.

*Flower size.*—An average of 2.7 cm in diameter and 7 mm in depth.

*Peduncles.*—An average of 4 mm in length and 1 mm in diameter, held at an average angle of 20° to lateral branches, moderately strong, 145B to 145C in color, surface sparsely pubescent.

*Pedicels.*—None.

*Flower buds.*—Globular in shape, an average of 5 mm in length and diameter prior to opening, color; 159D tinged with 56B to 56C, base 145B tinged with 183D.

*Sepals.*—10, 5 ovate and 5 oblong in shape, rotate arrangement, entire margin, acute apex, upper and lower surfaces; smooth and dull, ovate sepals; broadly cuneate base, an average of 5 mm in length and 4 mm in width, ovate sepals color; immature upper and lower surface 145B strongly tinged with 183D, mature upper surface 164B with base 150B, mature lower surface 183D, oblong sepals; cuneate base, an average of 7 mm in length and 2 mm in width, oblong sepals color; immature and mature upper surface 144B, immature and mature lower surface 145B.

*Calyx.*—Rotate, moderately reflexed, an average of 7 mm in length and 1.8 cm in diameter.

*Petals.*—An average of 5 per flower, self-cleaning, rotate arrangement, orbicular to broadly obovate in shape, upper and lower surface glabrous, dull, and slightly to moderately rugose, entire margin, cuneate base, obtuse apex, an average of 1 cm in length width, color; upper surface when opening 60A, lower surface when opening 160B, upper surface when fully open 60B lightly suffused with a blend between 65D and N155B more heavily at the petal base and veins, lower surface when fully open 160C, petal color slowly fades to a blend between 60D and 54A.

*Pistils.*—An average of 30, an average of 2 mm in length, stigma flattened in shape and 150B in color, style is an average of 1 mm in length and 0.5 mm in width, 150B in color, ovary is 145A in color and densely covered with short soft hairs 0.75 mm in length and 155A in color.

*Stamens.*—An average of 35, filaments are an average of 1.5 mm in length and 150B in color, anthers are flattened, ovate in shape, an average of 1 mm in length and 0.8 mm in width, 200C in color, pollen is low in quantity and 11A in color.

*Seed.*—None observed.

It is claimed:

1. A new and distinct cultivar of *Dasiphora* plant named 'Hachliss' as herein illustrated and described.

* * * * *